US00PP26083P3

(12) United States Plant Patent
Bennett

(10) Patent No.: US PP26,083 P3
(45) Date of Patent: Nov. 17, 2015

(54) ALMOND TREE NAMED 'BENNETT-HICKMAN'

(50) Latin Name: *Prunus dulcis*
Varietal Denomination: Bennett-Hickman

(76) Inventor: James Bennett, Hickman, CA (US)

( * ) Notice: Subject to any disclaimer, the term of this patent is extended or adjusted under 35 U.S.C. 154(b) by 20 days.

(21) Appl. No.: 13/065,340

(22) Filed: Mar. 17, 2011

(65) Prior Publication Data

US 2015/0113688 P1 Apr. 23, 2015

(51) Int. Cl.
*A01H 5/08* (2006.01)

(52) U.S. Cl.
USPC ..... Plt./155

(58) Field of Classification Search
USPC ..... Plt./155
CPC ..... A01H 5/0837; A01H 5/0825
See application file for complete search history.

*Primary Examiner* — Kent L Bell
(74) *Attorney, Agent, or Firm* — Mark D. Miller

(57) ABSTRACT

The invention provides a new and distinct variety of almond tree, named 'Bennett-Hickman', substantially as described and illustrated herein, which is somewhat similar to the 'Nonpareil' almond tree (unpatented), but which is distinguishable therefrom by possessing a heavier bloom, an extended bloom period, greener foliage that is retained for a longer duration of time, a sweeter kernel, with rare doubles, and a harvest period that runs approximately 14 days later than 'Nonpareil'.

1 Drawing Sheet

Latin name of the genus and species of the tree claimed: The tree claimed is known by the scientific name *Prunus dulcis.*

Variety denomination: The varietal denomination of the tree claimed is 'Bennett-Hickman'.

BACKGROUND OF THE NEW VARIETY

The present invention relates to a new and distinct variety of almond tree, botanically know as *Prunus dulcis*, which will hereby be denominated by the cultivar name 'Bennett-Hickman', and more specifically to an almond tree that produces a crop for harvesting and shipment approximately mid-August under the ecological conditions prevailing in the Modesto area of the San Joaquin Valley of central California.

'Bennett-Hickman' was discovered in 1975 as a seedling growing adjacent to a windmill on the inventor's property located in Hickman, Calif., in the San Joaquin Valley. The variety has been observed to have an extended and profuse bloom period and heavy nut production, as compared to the non-patented 'Nonpareil' variety. Asexual reproduction of the tree has produced progeny that are consistent with the original specimen as to vegetative characteristics.

ORIGIN AND ASEXUAL REPRODUCTION

The variety was discovered by Jim Bennett as a volunteer seedling adjacent to a cultivated area of his property located in Hickman, Calif. After approximately 3 years of observation, during which the variety's unusually long bloom period and heavy yields relative to the non-patented 'Nonpareil' variety were noted, the original seedling was asexually reproduced in 1979 by collecting budwood from the mother tree to bud on 'Nemaguard' rootstock at a Nursery in Hughson, Calif. Approximately 45 specimens were inter-planted throughout an orchard of 'Nonpareil' trees and other commercial varieties. All of these trees have survived.

Reproduction by budding and grafting resulted in true-to-type progeny with respect to all tree vegetative and reproductive characteristics. These reproductions utilized 'Nemaguard' rootstock on which the present variety was compatible and true to the original tree in all respects.

The presently observed reproduced specimens are now in their 8th leaf.

SUMMARY OF THE VARIETY

The present variety was selected and tested because of its extended and profuse bloom period and heavy nut production and has the following outstanding and distinguishing characteristics when grown under normal horticultural practices in the Modesto area of the San Joaquin Valley of central California. Tree foliage is greener in color than the leaves of 'Nonpareil' and the harvest date of 'Bennett-Hickman' is approximately 14 days later than 'Nonpareil'. Furthermore, the 'Bennett-Hickman' variety holds it leaves approximately 14 days longer than the 'Nonpareil' variety on an average year. Nut yield of the new variety is on average slightly greater than that of the 'Nonpareil' variety, and nut quality is comparable to 'Nonpareil'. The variety blooms about 7 days earlier than 'Nonpareil', has an abundance of flowers along each fruiting branch, and continues to bloom about 7 days longer than 'Nonpareil'. The extended blooming characteristics make it a very attractive pollinator for use with 'Nonpareil', as well as other varieties.

Molecular analysis of the S-allele controlling cross-incompatibility in almond testing was performed and indicates that the 'Bennett-Hickman' variety would be placed in the Thompson cross-incompatibility group. This means the variety is cross-compatible with most commercial California varieties including 'Nonpareil' (unpatented) and 'Carmel' (U.S. Plant Pat. No. 2,641). Field test crosses performed in 2009 provide additional confirmation of the cross-compatibility of 'Bennett-Hickman' with the 'Nonpareil' variety.

DESCRIPTION OF THE PHOTOGRAPHS

The new almond tree variety is illustrated by the accompanying photograph which shows a fruiting branch of the present variety displaying its bearing characteristics, an apical twig and examples of intact and split hulls and nuts and kernels, all typical of the variety.

The colors shown are as true as can be reasonably obtained by conventional photographic procedures.

The samples depicted in the photograph are taken from trees that are in their 8th year, grown utilizing 'Nemaguard' rootstock, under the ecological conditions prevailing in the Modesto area of the San Joaquin Valley of central California.

FIG. 1 shows a fruiting branch, an apical twig and examples of intact and split hulls, nuts and kernels.

DETAILED BOTANICAL DESCRIPTION OF THE NEW VARIETY

Referring now more specifically to the pomological characteristics of this new and distinct variety of almond tree, the following has been observed under the ecological conditions prevailing in Hickman Calif., which is near Modesto, Calif. (San Joaquin Valley). Observations were performed just prior to the harvest stage on Aug. 18, 2009 and at the flowering stage on Feb. 16, 2010.

All major color code designations are by reference to the Inter-Society Color Council, National Bureau of Standards. Common color names are also used.

NOT A COMMERCIAL WARRANTY

The following detailed description has been prepared to solely comply with the provisions of 35 U.S.C. §112, and does not constitute a commercial warranty, (either expressed or implied), that the present variety will in the future display the botanical or other varietal characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

TREE

*Origin*.—The present variety was discovered as an open pollinated seedling of unknown parentage growing within the cultivated region adjacent to the inventor's orchard which is located in Hickman, Calif.

*Vigor*.—Considered very vigorous.

*Hardiness*.—Considered hardy under typical San Joaquin Valley climatic conditions.

*Chilling requirement*.—Considered normal under prevailing San Joaquin Valley climatic conditions.

*Tree form*.—Considered spreading and upright in its growth pattern. For observed trees that were 8 years old, when grown on 'Nemaguard' rootstock, the height of the trees were approximately 15 feet. Further, these same trees had a crown spread of approximately 22 feet.

*Productivity*.—Considered very productive. For trees that are at least 8 years old, with currently acceptable planting densities, approximately 3000 pounds of almonds on average are harvested per acre.

*Regularity of bearing*.—Considered regular for the species. No significant alternate bearing has been observed.

*Fertility*.—Self-sterile. The new variety must be cross pollinated by other almond varieties, including 'Nonpareil' (unpatented) and 'Carmel' (U.S. Plant Pat. No. 2,641).

*Date of harvest*.—Sep. 7, 2009, approximately 14 days later than 'Nonpareil' when irrigated using microsprinklers.

TRUNK

*Size*.—Considered large, approximately 29.50 inches in circumference when measured at a distance of about 16 inches above the surface of the earth on trees which are at least 8 years old.

*Bark texture*.—Considered moderately rough.

*Bark color*.—Dark olive green [126. d.OlG].

*Bark lenticels*.—This characteristic is not distinctive of the present variety.

BRANCHES

*Size*.—Considered large for the species, approximately 54.25 inches in circumference when measured at a distance of approximately 12 inches above the crotch of an 8 year old tree.

*Surface texture*.—Immature branches — Considered smooth.

*Surface texture*.—Mature branches — Considered rough. As wood becomes older, texture becomes rougher with accumulation of lenticels.

*Bark color*.—Immature branches — Topside of first year wood is Grayish brown [61. gy.Br]. Underside of first year wood is Light olive gray [112. lOlGr].

*Bark color*.—Mature branches — Moderate olive green [125. M.OlG].

*Lenticels*.—Number, Size and Shape — Approximately 4 to 8 per square inch and 2 to 4 mm in length, and 1 mm in width. Shape linear. Color - Dark yellow [88. d.Y].

LEAVES

*Size*.—Considered medium for the species, approximately 90 mm in length; and about 15 mm. to about 22 mm. in width.

*Leaf shape*.—Considered lanceolate. Leaf Apex — Considered acuminate. Leaf Base — Considered acute.

*Leaf thickness*.—Considered normal for species.

*Leaf color*.—Upwardly facing surfaces — Moderate yellowish green [136. m.YG].

*Leaf color*.—Downwardly facing surfaces — Deep yellow green [118. d.YG].

*Leaf marginal form*.—Finely serrated.

*Leaf vein*.—Pinnately veined. Color — Vivid yellowish green [115. v.YG].

*Leaf petiole*.—Length — About 11 mm. to about 26 mm. Leaf Petiole. — Thickness — About 1 mm.

*Leaf petiole*.—Color — Vivid yellowish green [115. v.YG].

*Leaf stipules*.—Very inconspicuous and predominately absent.

FLOWERS

*Date of full bloom*.—Feb. 18, 2010 under the ecological conditions prevailing near Modesto, Calif.
*Bloom amount*.—Typically 5 flowers per cluster.
*Bloom color*.—Upper and lower petal surfaces are the same. Petal base is deep purplish pink [248. d.PurP] while the majority of the petal is pinkish white [9. p.W].
*Flower diameter*.—Average 41.6 mm.
*Flower depth*.—Averages 15.5 mm from the base of the ovary to the tip of the stigma.
*Petals*.—Marginal form — Considered obovate with widespread apex notching.
*Petals*.—Length — Average 17.9 mm.
*Petals*.—Width — Average 12.0 mm.
*Petal margin*.—Undulate.
*Petal base*.—Obtuse.
*Petals*.—Number — Generally 5.
*Sepals*.—Color — Upper surface: vivid yellowish green [115. v.YG] with strong purplish red [255. s.PurR] venation. Lower surface: Strong yellow green [117. s.YG] with very deep reddish purple [239. v.d.RP] venation.
*Size of individual sepals*.—Average 6.2 mm. in length and about 3.7 mm. in width.
*Sepals*.—Shape — Conic.
*Sepals*.—Number — Generally 5.
*Sepal margin*.—Entire.
*Sepal apex*.—Tapering to a point.
*Pistil*.—Length — Average 14.7 mm.
*Anthers*.—Color — Light yellow [86. l.Y].
*Pollen production*.—Abundant.
*Pollen color*.—Brilliant yellow [83. brill.Y].
*Stamens*.—Length — About 5.7 mm. to about 10.4 mm.
*Style color*.—Light yellow [86. l.Y].
*Style length*.—About 8.0 mm. to about 12.0 mm.
*Stigma color*.—Deep yellow [85. d.Y].
*Ovary shape*.—Ovate.
*Ovary color*.—Brilliant yellow green [116. b.YG] with heavy pubescence.
*Pedicel*.—Length — About 2 mm. to about 3 mm.
*Pedicel*.—Width — Average 1 mm.
*Pedicel*.—Color — Brilliant yellow green [116. brill.YG].
*Flower buds*.—Diameter — Average 6.2 mm.
*Flower buds*.—Length — Average 13.7 mm.
*Flower buds*.—Shape — Considered conic.
*Flower buds*.—Color — Pinkish white [9. p.W].
*Fragrance*.—Moderate fragrance that is honey-like.

CROP

*Bearing*.—On average the nut yield of the new variety is slightly greater than that of the 'Nonpareil' variety.
*Productivity*.—Considered very productive for trees that are 8 years old.
*Hull*.—Texture — Pubescent.
*Hull*.—Form — Considered ovate.
*Hull*.—Thickness — About 2 mm to about 3 mm.
*Hull*.—Color — Outer color at splitting: Strong yellow green [117. s.YG]; suture color at splitting: Brilliant yellow green [116. b.YG].
*Dehiscence*.—Opens freely.
*Splitting*.—Complete along suture.

NUT

*Nut size*.—Generally — Length — Average 34 mm; Width — Average 21 mm.
*Shape*.—Considered ovate.
*Thickness*.—About 15 mm.
*Outer shell*.—Form — Considered flaked and brittle.
*Color*.—Shell color at splitting varies from light yellow [86. l.Y] to moderate yellow [87. m.Y].
*Pits*.—Small, scattered and numerous.
*Wing*.—Average protrusion is 3 mm from surface of nut tapering at the base and apex.

KERNEL

*Size*.—Length — Average 25 mm; Width — Average 13 mm.
*Shape*.—Ovate.
*Kernel thickness*.—Average 10 mm at hull splitting.
*Stem scar*.—Not readily apparent.
*Apex*.—Shape — Considered acute.
*Surface texture*.—Slightly ribbed along veins with slight pubescence.
*Pubescence*.—Considered slight.
*Color*.—Skin color at splitting Deep yellow [85. d.Y]; vein color at splitting Light olive brown [94. 1.OlBr].
*Numbers of doubles produced*.—Considered rare; average is 1% which is considered very good as the amount of doubles produced by the 'Nonpareil' almond trees (unpatented) which are growing in the same geographical location.
*Kernel flavor*.—Sweet; sweeter than 'Nonpareil' and 'Carmel' varieties, which are growing in the same geographical location.
*Keeping quality*.—Considered good.
*Keeping and shipping quality*.—Considered good for the variety.
*Average kernel weight*.—About 1.13 grams average weight per kernel.

The present variety may be processed as a whole, blanched, sliced or diced product and is an excellent natural, salted or roasted nut.

Although this new variety of almond tree possess the described characteristics noted above as a result of the growing conditions prevailing in the Modesto area in the San Joaquin Valley of Central California, it is understood that variations of the usual magnitude and characteristics incident to changes in growing conditions, fertilization, pruning and pest control are to be expected.

I claim:

1. A new and distinct variety of almond tree, named 'Bennett-Hickman', substantially as described and illustrated herein, which is somewhat similar to the 'Nonpareil' almond tree (unpatented), but which is distinguishable therefrom by possessing a heavier bloom, an extended bloom period, greener foliage that is retained for a longer duration of time, a sweeter kernel, with rare doubles, and a harvest period that runs approximately 14 days later than 'Nonpareil'.

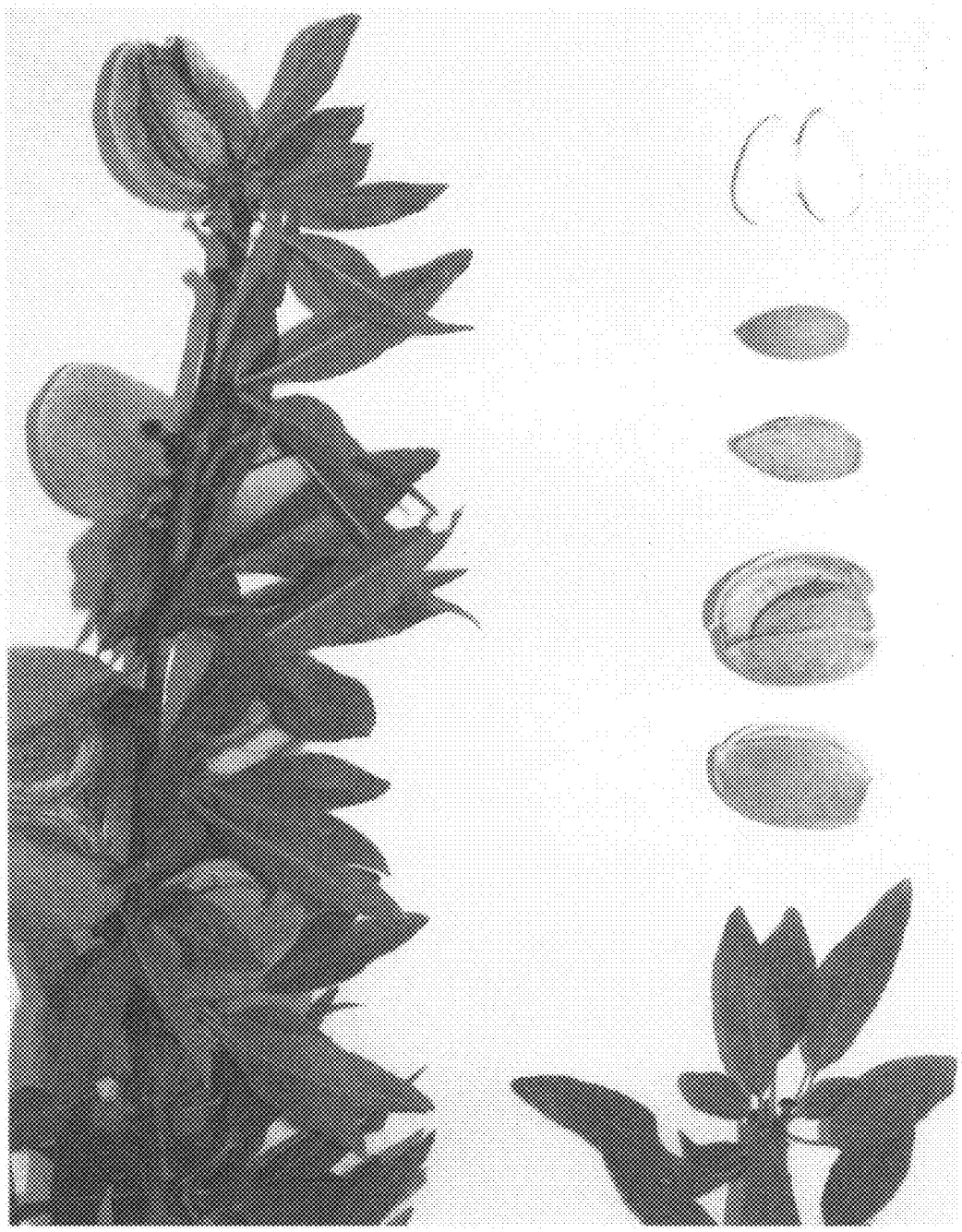

* * * * *